United States Patent
Hillairet et al.

(10) Patent No.: US 7,754,835 B2
(45) Date of Patent: Jul. 13, 2010

(54) POLYMERISATION OF ETHYLENE AND ALPHA-OLEFINS WITH PHOSPHINO-IMINOPHENOL COMPLEXES

(75) Inventors: Caroline Hillairet, Soignies (BE); Guillaume Michaud, Lille (FR); Sabine Sirol, Horrues (BE)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 0 days.

(21) Appl. No.: 12/282,252

(22) PCT Filed: Mar. 7, 2007

(86) PCT No.: PCT/EP2007/052111

§ 371 (c)(1),
(2), (4) Date: Jan. 29, 2009

(87) PCT Pub. No.: WO2007/104679

PCT Pub. Date: Sep. 20, 2007

(65) Prior Publication Data

US 2009/0240011 A1    Sep. 24, 2009

(30) Foreign Application Priority Data

Mar. 10, 2006 (EP) ................... 06110967

(51) Int. Cl.
*C08F 4/22* (2006.01)

(52) U.S. Cl. ............ 526/172; 526/943; 528/410; 528/423; 528/425; 502/121; 502/125

(58) Field of Classification Search ............ 526/172, 526/943; 528/410, 423, 425; 502/121, 125
See application file for complete search history.

(56) References Cited

FOREIGN PATENT DOCUMENTS

EP    1574529 A1    9/2005

OTHER PUBLICATIONS

Bhattacharyya, Pravat, et al., "Synthesis of New Heterotridentate Ligands Comprising Mixed Hard-Soft Donor Sets, and Their Complexation with Group 10 Metals," Journal of Chemical Society, Dalton Translation, 1998, pp. 3609-3614.

Bluhm, Martin E., et al., "Chromium Imine and Amine Complexes as Homogeneous Catalysts for the Trimerisation and Polymerisation of Ethylene," Journal of Organometallic Chemisty 690, 2005, pp. 713-721.

Dilworth, Jonathan R., et al., "Complexes for Functionalised Phosphine Ligands, Part 1, Complexes of FeIII, CoIII, NiII and ReV with Tridentate Schiff Bases Having PNO, NNO and NNS Donor Sets, Crystal Structures of 2-(Ph2PC6H4N=CH)C6H4OH and [CO(2-Ph2PC6H4CH=N)C6H4O)2][PF6]+," Journal of Chemical Society, Dalton Translation, 1994, Issue 1, pp. 3553-3562.

*Primary Examiner*—Ling-Siu Choi
*Assistant Examiner*—Sonya Wright
(74) *Attorney, Agent, or Firm*—Tenley R. Krueger

(57) ABSTRACT

The present invention relates to the field of single site catalyst systems based on phosphino-iminophenol complexes that are suitable for oligomerising or polymerising ethylene and alpha-olefins.

13 Claims, 2 Drawing Sheets

Figure 1:
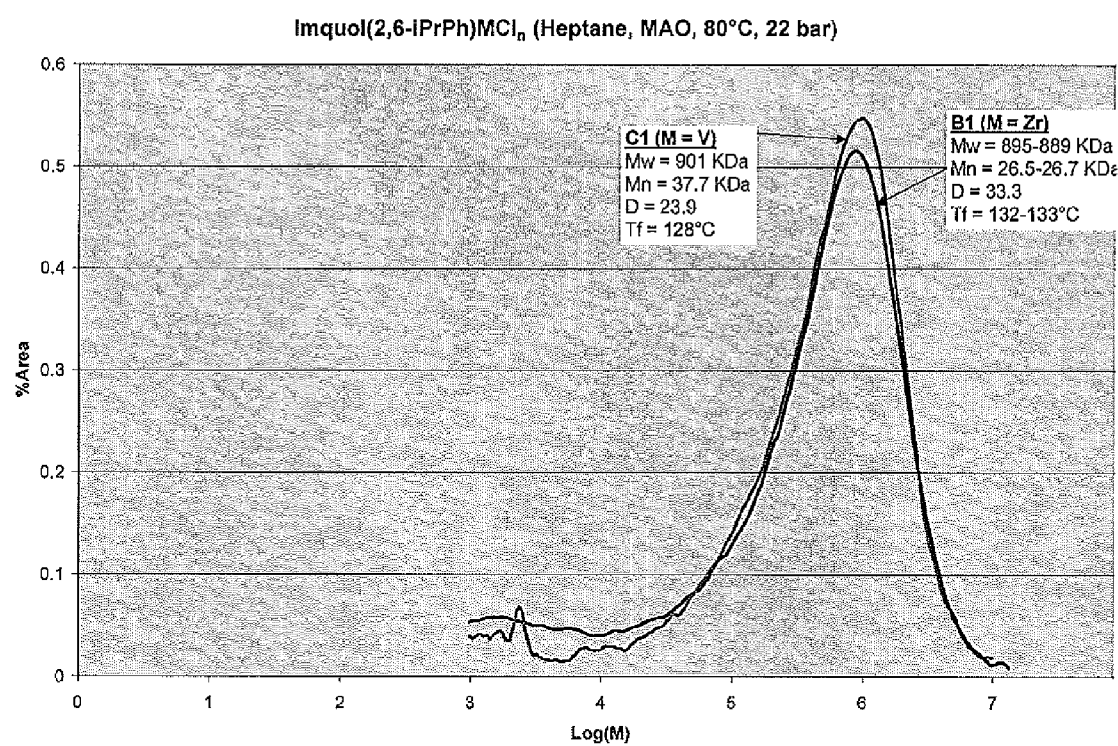
Figure 2:
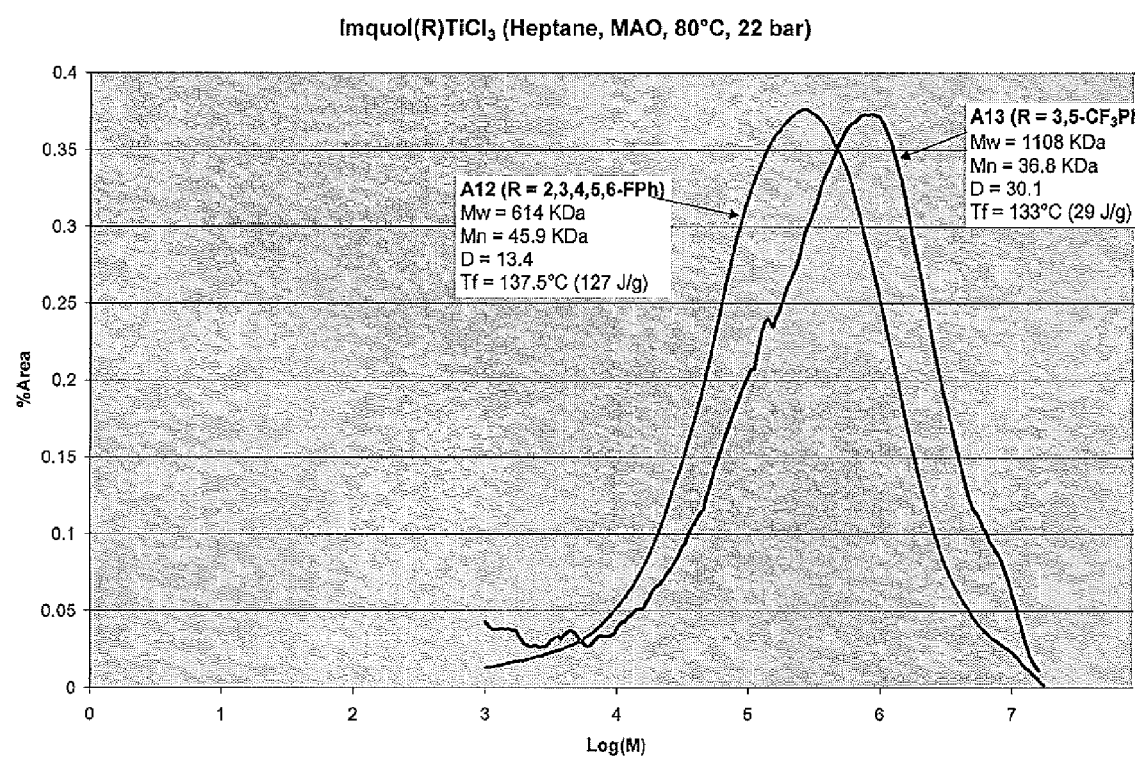

POLYMERISATION OF ETHYLENE AND ALPHA-OLEFINS WITH PHOSPHINO-IMINOPHENOL COMPLEXES

The present invention relates to the field of single site catalyst systems based on phosphino-iminophenol complexes and suitable for oligomerising or polymerising ethylene and alpha-olefins.

A multitude of catalyst systems available for polymerising or oligomerising ethylene and alpha-olefins exist, but there is a growing need for finding new systems capable of tailoring polymers with very specific properties. More and more post-metallocene catalyst components based on early or late transition metals from Groups 3 to 10 of the Periodic Table have recently been investigated such as for example those disclosed in Gibson and al. review (Gibson, V. C.; Spitzmesser, S. K., in Chem. Rev. 2003, 103, p. 283). But there is still a need to improve either the specificities or the performances of these systems.

Phosphorus containing ligands were studied for olefin polymerisation. Imino-phosphine group 10 complexes are mainly active towards olefin oligomerisation (Feringa et al., in WO 98/42440; Feringa et al., in Chem. Comm. 1998, p 223). Anionic tridentate [PNO] group IV catalysts show moderate activity for ethylene polymerisation (Organometallics 2004, 23, p 1684).

Schiff bases derivatives of phosphino-carboxaldehyde and 2-aminophenol or amino-alcool are known in the literature (J. Dilworth et al. in J. Chem. Soc. Dalton Trans. Inorg. Chem. 1994, p 3553; H. Brunner et al. in Eur. J. Inorg. Chem. 1999, p 51; H. Brunner et al. in Eur. J. Inorg Chem. 1998, p 43), but corresponding complexes have never been described as catalysts for polymerisation of olefins.

The aim of this invention is to provide new single site catalysts based on tridentate phosphorus ligands active in olefin polymerisation.

It is another aim of the present invention to provide active catalyst systems based on these catalyst components.

It is a further aim of the present invention to provide a process for polymerising or for oligomerising ethylene and alpha-olefins with these new catalyst systems.

Accordingly, the present invention discloses ligands of general formula I or II

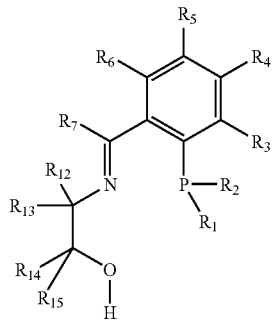

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{15}$ are each independently selected from hydrogen, unsubstituted or substituted hydrocarbyl having from 1 to 20 carbon atoms, or inert functional group. Two or more of those groups can themselves be linked together to form further ring or rings.

Preferably, $R_1$ and $R_2$ are the same or different and are unsubstituted or substituted alkyl groups, unsubstituted or substituted aryl groups, or unsubstituted or substituted cycloalkyl groups having at most 12 carbon atoms, more preferably, they are the same and are unsubstituted phenyl groups.

$R_3$, $R_4$, $R_5$, $R_6$ and $R_7$, are each independently selected from hydrogen, unsubstituted or substituted hydrocarbyl having from 1 to 20 carbon atoms, or inert functional group. Two or more of those groups can themselves be linked together to form further ring or rings. Preferably, they are all hydrogen.

$R_8$, $R_9$, $R_{10}$ and $R_{11}$ are each independently selected from hydrogen, unsubstituted or substituted hydrocarbyl having from 1 to 20 carbon atoms, or inert functional group. Two or more of those groups can themselves be linked together to form further ring or rings Preferably, $R_8$, $R_{10}$ and $R_{11}$ are hydrogen or methyl and $R_9$ is hydrogen, methyl, tert-butyl, phenyl, nitro or chlorine, more preferably is $R_9$ phenyl.

$R_{12}$, $R_{13}$, $R_{14}$ and $R_{15}$ are the same or different, hydrogen, unsubstituted or substituted alkyl groups, unsubstituted or substituted aryl groups, or unsubstituted or substituted cycloalkyl groups, all these groups having at most 20 carbon atoms, preferably at most 10 carbon atoms, more preferably at most 6 carbon atoms. $R_{12}$, $R_{13}$, $R_{14}$ and $R_{15}$ can be linked together to form a ring.

The present invention also discloses catalyst components of formula III and IV

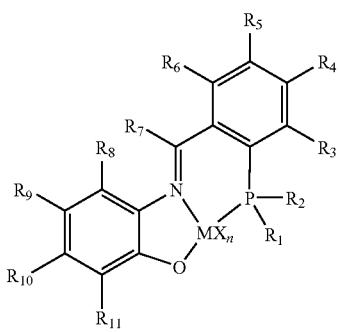

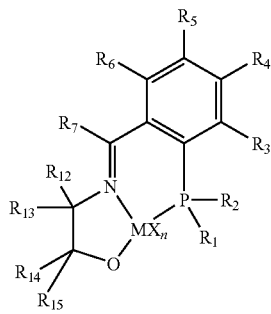

IV resulting respectively from the complexation of ligands I and II with metallic salt $MX_{n+1}$ in a solvent, wherein $R_1$ to $R_{15}$ are as described hereabove, M is a metal Group 3 to 10 of the Periodic Table, each X can be the same or different and is selected from halogen, substituted or unsubstituted hydrocarbyl having from 1 to 20 carbon atoms, substituted or unsubstituted aryloxy or alkoxy, and (n+1) is the valence of M.

Preferably M is Ti, Zr, Hf, V, Cr, Mn, Fe, Co, Ni, Pd or rare earths. More preferably, it is Ti, Cr or Fe.

Preferably X is halogen, more preferably it is chlorine.

The solvent may be selected from dichloromethane or tetrahydrofuran and the complexation reaction is carried out at room temperature or at reflux.

The present invention further discloses an active catalyst system comprising the single site catalyst component of formula III or IV and an activating agent having an ionising action.

Suitable activating agents are well known in the art. The activating agent can be an aluminium alkyl represented by formula $AlR^+_n X_{3-n}$ wherein $R^+$ is an alkyl having from 1 to 20 carbon atoms and X is a halogen. The preferred alkylating agents are triisobutyl aluminium (TIBAL) or triethyl aluminium (TEAL).

Alternatively, it can be aluminoxane and comprise oligomeric linear and/or cyclic alkyl aluminoxanes represented by formula

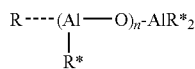

for oligomeric, linear aluminoxanes and by formula

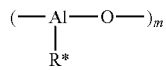

for oligomeric, cyclic aluminoxane,
wherein n is 1-40, preferably 10-20, m is 3-40, preferably 3-20 and R* is a $C_1$-$C_8$ alkyl group and preferably methyl.

The amount of activating is selected to give an Al/M ratio of from 100 to 3000, preferably of about 2000.

Suitable boron-containing activating agents may comprise a triphenylcarbenium boronate such as tetrakis-pentafluorophenyl-borato-triphenylcarbenium as described in EP-A-0427696, or those of the general formula [L'-H]+ [$BAr_1Ar_2X_3X_4$]— as described in EP-A-0277004 (page 6, line 30 to page 7, line 7). The amount of boron-containing activating agent is selected to give B/M ratio of from 0.5 to 5, preferably of about 1.

In another embodiment, according to the present invention, the single site catalyst component of formula III or IV may be deposited on a conventional support. Preferably, the conventional support is silica impregnated with MAO. Alternatively and preferably, it can be an activating support such as fluorinated alumina silica.

The present invention further discloses a method for preparing an active catalyst system that comprises the steps of:
 a) providing a ligand of formula I or II;
 b) complexing the ligand of step a) with a metallic salt $MX_{n+1}$ in a solvent;
 c) retrieving respectively the catalyst component III or IV;
 d) activating with an activating agent having an ionising action;
 e) optionally adding a cocatalyst;
 f) retrieving an active oligomerisation or polymerisation catalyst system.

Alternatively, in step d) catalyst component III or IV is deposited on a support impregnated with an activating agent.

The cocatalyst may be selected from triethylaluminium, triisobutylaluminum, tris-n-octylaluminium, tetraisobutyl-dialuminoxane or diethyl zinc.

The active catalyst system is used in the oligomerisation and in the polymerisation of ethylene and alpha-olefins.

The present invention discloses a method for the oligomerisation or the homo- or co-polymerisation of ethylene and alpha-olefins that comprises the steps of:
 a) injecting the active catalyst system into the reactor;
 b) injecting the monomer and optional comonomer;
 c) maintaining under polymerisation conditions;
 d) retrieving the oligomers and/or polymer.

The pressure in the reactor can vary from 0.5 to 50 bars, preferably from 5 to 25 bars.

The polymerisation temperature can range from 10 to 100° C., preferably from 50 to 85° C.

Preferably the monomer and optional comonomer are selected from ethylene, propylene or 1-hexene.

In another preferred embodiment according to the present invention, the optional comonomer is a polar functionalised alpha-olefin.

EXAMPLES

All reactions were performed using standard Schlenk techniques or in an argon-filled glove-box. The starting materials and reagents, purchased from commercial suppliers, were used without purification. All the solvents were dried and distilled before use either over sodium and benzophenone for toluene, pentane and THF, or over $CaH_2$ for ethanol. 2-diphenylphosphinobenzaldehyde was synthesized according to the procedure reported in Inorganic Synthesis 1982, Vol 21, 175. $^1H$, $^{13}C$ and $^{31}P$ NMR spectra were recorded on a Bruker Advance500.

Preparation of Ligands

Synthesis of
2-[(2-diphenylphosphino)benzylimino]-phenol (L1)

290 mg (1 mmol) of 2-diphenylphosphinobenzaldehyde dissolved in 5 mL of ethanol were added dropwise to 131 mg (1.2 mmol) of 2-aminophenol dissolved in 5 mL of ethanol. The yellow solution was stirred under reflux at a temperature of 90° C. for 2 hours. The solution was cooled to room temperature. The solution was then concentrated under vacuum. The surpernatant was filtered off and the solid was washed with cold ethanol, and dried under vacuum. 218 mg of Ligand L1 were obtained as orange solid with a yield of 57%.

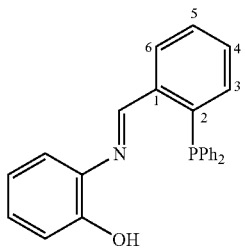

L1

NMR results were as follows.

$^1$H NMR (500 MHz, CDCl$_3$) δ (ppm): 6.85 (t, 1H, J$_{HH}$=8 Hz, J$_{PH}$=1.2 Hz, H4 Phenol), 6.96 (d, 1H, J$_{HH}$=8 Hz, J$_{PH}$=1 Hz, H6 Phenol), 7.02 (m, H3), 7.10 (d, 1H, J$_{HH}$=8 Hz, J$_{PH}$=1.2 Hz, H3 Phenol), 7.16 (t, 1H, J$_{HH}$=8 Hz, J$_{PH}$=1.2 Hz, H5 Phenol), 7.22 (d, 1H, J$_{PH}$=1.8 Hz, OH), 7.30 (m, 4H, H ortho PPh$_2$), 7.37 (m, 7H, H meta and para PPh$_2$ and H4), 7.52 (t, 1H, J$_{HH}$=7.7 Hz, J$_{PH}$=0.7 Hz, H5), 8.01 (m, 1H, H6), 9.04 (d, 1H, J$_{PH}$=4 Hz, CH=N).

$^{13}$C{$^1$H} NMR (125 MHz, CDCl$_3$) δ (ppm): 115.5 (C6 Phenol), 116.5 (C4 Phenol), 120.3 (C3 Phenol), 129.0 (d, 4C, J$_{PC}$=7 Hz, CH meta PPh$_2$), 129.2 (C5 Phenol and C6), 129.3 (CH para PPh$_2$), 131.1 (C5), 131.3 (d, J$_{PC}$=4 Hz, C4), 134.3 (d, 4C, J$_{PC}$=20 Hz, CH ortho PPh$_2$), 134.9 (C3), 136.2 (C—N), 137.3 (d, 2C, J$_{PC}$=8.5 Hz, C ipso PPh$_2$), 138.6 (d, J$_{PC}$=21 Hz, C1), 139.2 (d, J$_{PC}$=15 Hz, C2), 152.5 (C—OH), 156.9 (d, J$_{PC}$=11 Hz, CH=N).

$^{31}$P{$^1$H, $^{13}$C} NMR (202 MHz, CDCl$_3$) δ (ppm): −7.5.

Synthesis of 2-[(2-diphenylphosphino)benzylimino]-3-methyl-phenol (L2)

The procedure was the same as that used for preparing L1 except that 123 mg of 2-amino-3-methylphenol (1 mmol) were used as reagent. 273 mg of ligand L2 were obtained as yellow solid with a yield of 67%.

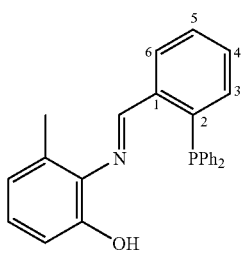

L2

The NMR results were as follows.

$^1$H NMR (500 MHz, CD$_2$Cl$_2$) δ (ppm): 2.00 (s, 3H, CH$_3$), 6.60 (d, 1H, J$_{HH}$=7.6 Hz, H6 Phenol) 6.65 (d, 1H, J$_{HH}$=7.9 Hz, H4 Phenol), 6.80 (s, 1H, OH), 6.86 (t, 1H, J$_{HH}$=7.8 Hz, H5 Phenol), 6.96 (m, 1H, H3), 7.20 (m, 4H, H ortho PPh$_2$), 7.27 (m, 6H, H meta and para PPh$_2$), 7.32 (t, 1H, J$_{HH}$=7.6 Hz, H4), 7.45 (t, 1H, J$_{HH}$=7.6 Hz, H5), 7.91 (m, 1H, H6), 8.80 (d, 1H, J$_{PH}$=4 Hz, CH=N).

$^{13}$C{$^1$H} NMR (125 MHz, CD$_2$Cl$_2$) δ (ppm): 18.6 (CH$_3$), 112.6 (C6 phenol), 122.9 (C4 phenol), 126.5 (C5 phenol), 127.9 (C-Me), 129.0 (d, 4C, J$_{PC}$=7 Hz, CH meta PPh$_2$), 129.2 (C6), 129.3 (2C, CH para PPh$_2$), 131.0 (d, J$_{PC}$=4 Hz, C4), 131.3 (C5), 134.2 (d, 4C, J$_{PC}$=20 Hz, CH ortho PPh$_2$), 134.9 (C3), 137.2 (C—N), 137.4 (d, 2C, J$_{PC}$=7 Hz, C ipso PPh$_2$), 138.6 (d, J$_{PC}$=20 Hz, C1), 139.3 (d, J$_{PC}$=16 Hz, C2), 150.2 (C—OH), 163.2 (d, J$_{PC}$=10 Hz, CH=N).

$^{31}$P{$^1$H, $^{13}$C} NMR (202 MHz, CD$_2$Cl$_2$) δ (ppm): −7.7.

Synthesis of 2-[(2-diphenylphosphino)benzylimino]-4-methyl-phenol (L3)

The procedure was the same as that used for preparing L1 except that 123 mg of 2-amino-4-methylphenol (1 mmol) were used as reagent. 192 mg of ligand L3 were obtained as orange solid with a yield of 47%.

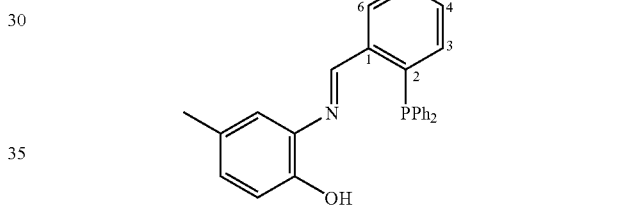

L3

The NMR results were as follows.

$^1$H NMR (500 MHz, CD$_2$Cl$_2$) δ (ppm): 2.18 (s, 3H, CH$_3$), 6.70 (d, 1H, J$_{HH}$=8.2 Hz, H6 Phenol), 6.80 (d, 1H, J$_{PH}$=1.2 Hz, OH), 6.87 (dd, 1H, J$_{HH}$=8.2 Hz, J$_{PH}$=1 Hz, H5 Phenol), 6.93 (m, 1H, H3), 7.07 (d, 1H, J$_{PH}$=2.8 Hz, H3 Phenol), 7.22 (m, 4H, H ortho PPh$_2$), 7.28 (m, 7H, H meta and para PPh$_2$ and H4), 7.44 (td, 1H, J$_{HH}$=7.4 Hz, J$_{PH}$=1 Hz, H5), 7.92 (m, 1H, H6), 8.90 (d, 1H, J$_{PH}$=3.6 Hz, CH=N).

$^{13}$C{$^1$H} NMR (125 MHz, CD$_2$Cl$_2$) δ (ppm): 20.7 (CH$_3$), 114.9 (C6 Phenol), 116.9 (C3 Phenol), 129.0 (d, 4C, J$_{PC}$=7 Hz, CH meta PPh$_2$), 129.2 (C6), 129.3 (2C, CH para PPh$_2$), 129.7 (C5 Phenol and C—CH$_3$), 130.9 (C5), 131.5 (d, J$_{PC}$=4 Hz, C4), 134.3 (d, 4C, J$_{PC}$=20 Hz, CH ortho PPh$_2$), 134.9 (C3), 135.8 (C—N), 137.6 (d, 2C, J$_{PC}$=9 Hz, C ipso PPh$_2$), 138.5 (d, J$_{PC}$=21 Hz, C1), 139.3 (d, J$_{PC}$=15 Hz, C2), 156.9 (C—OH), 159.6 (d, J$_{PC}$=9 Hz, CH=N).

$^{31}$P{$^1$H, $^{13}$C} NMR (202 MHz, CD$_2$Cl$_2$) δ (ppm): −6.8.

Synthesis of 2-[(2-diphenylphosphino)benzylimino]-5-methyl-phenol (L4)

The procedure was the same as that used for preparing L1 except that 123 mg of 2-amino-5-methylphenol (1 mmol) were used as reagent. 303 mg of ligand L4 were obtained as orange solid with a yield of 74%.

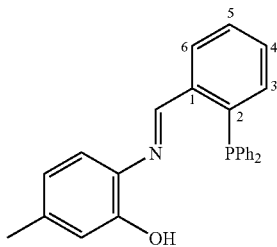

L4

The NMR results were as follows.

$^1$H NMR (500 MHz, CD$_2$Cl$_2$) δ (ppm): 2.21 (s, 3H, CH$_3$), 6.57 (d, 1H, J$_{HH}$=8.1 Hz, H4 Phenol), 6.66 (s, 1H, H6 Phenol), 6.92 (m, 1H, H3), 6.94 (d, 1H, J$_{HH}$=8.1 Hz, H3 Phenol), 7.21 (m, 4H, H ortho PPh$_2$), 7.27 (m, 8H, H meta and para PPh$_2$ and H4 and OH), 7.43 (t, 1H, J$_{HH}$=7.6 Hz, H5), 7.90 (m, 1H, H6), 8.92 (d, 1H, J$_{PH}$=3.6 Hz, CH=N).

$^{13}$C{$^1$H} NMR (125 MHz, CD$_2$Cl$_2$) δ (ppm): 21.5 (CH$_3$), 115.9 (C4 Phenol and C6 Phenol), 121.7 (C3 Phenol), 129.0 (d, 4C, J$_{PC}$=7 Hz, CH meta PPh$_2$) 129.2 (C6), 129.3 (2C, CH para PPh$_2$), 130.9 (C5), 131.4 (d, J$_{PC}$=4 Hz, C4), 133.5 (C—CH$_3$), 134.3 (d, 4C, J$_{PC}$=20 Hz, CH ortho PPh$_2$), 134.9 (C3), 137.6 (d, 2C, J$_{PC}$=9 Hz, C ipso PPh$_2$), 137.3 (d, J$_{PC}$=21 Hz, C1), 139.4 (d, J$_{PC}$=15 Hz, C2), 139.9 (C—N), 152.5 (C—OH), 155.8 (d, J$_{PC}$=9 Hz, CH=N).

$^{31}$P{$^1$H, $^{13}$C} NMR (202 MHz, CD$_2$Cl$_2$) δ (ppm): −7.0.

Synthesis of 2-[(2-diphenylphosphino)benzylimino]-4-tertbutyl-phenol (L5)

The procedure was the same as that used for preparing L1 except that 165 mg of 2-amino-5-tertbutylphenol (1 mmol) were used as reagent. 272 mg of ligand L5 were obtained as yellow solid with a yield of 60%.

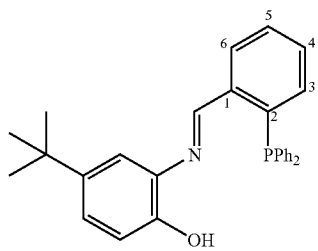

L5

The NMR results were as follows.

$^1$H NMR (500 MHz, CD$_2$CO$_2$) δ (ppm): 1.21 (s, 9H, tBu), 6.75 (d, 1H, J$_{HH}$=8.5 Hz, H6 Phenol), 6.93 (m, 1H, H3), 7.00 (d, 1H, J$_{PH}$=2.2 Hz, OH), 7.06 (d, 1H, J$_{PH}$=2.6 Hz, H3 Phenol), 7.09 (dd, 1H, J$_{HH}$=8.5 Hz, J$_{PH}$=2.2 Hz, H5 Phenol), 7.22 (m, 4H, H ortho PPh$_2$), 7.29 (m, 7H, H meta and para PPh$_2$ and H4), 7.44 (t, 1H, J$_{HH}$=7.2 Hz, H5), 7.93 (m, 1H, H6), 8.92 (d, 1H, J$_{PH}$=3.5 Hz, CH=N).

$^{13}$C{$^1$H} NMR (125 MHz, CD$_2$Cl$_2$) δ (ppm): 31.6 (CH$_3$), 34.6 (C—(CH$_3$)$_3$), 113.3 (C6 phenol), 114.6 (C3 phenol), 126.2 (C5 phenol), 129.0 (d, 4C, J$_{PC}$=7 Hz, CH meta PPh$_2$), 129.2 (C6), 129.3 (CH para PPh$_2$), 130.9 (C5), 131.5 (d, J$_{PC}$=4 Hz, C4), 134.3 (d, 4C, J$_{PC}$=20 Hz, PPh$_2$), 134.9 (C3), 135.5 (C—N), 137.6 (d, 2C, J$_{PC}$=9 Hz, C ipso PPh$_2$), 138.4 (d, J$_{PC}$=21 Hz, C1), 139.2 (d, J$_{PC}$=15 Hz, C2), 143.3 (C-tBu), 150.0 (C—OH), 156.9 (d, J$_{PC}$=9 Hz, CH=N).

$^{31}$P{$^1$H, $^{13}$C} NMR (202 MHz, CD$_2$Cl$_2$) δ (ppm): −6.5.

Synthesis of 2-[(2-diphenylphosphino)benzylimino]-4-phenyl-phenol (L6)

The procedure was the same as that used for preparing L1 except that 185 mg of 2-amino-4-phenylphenol (1 mmol) were used as reagent. 399 mg of ligand L6 were obtained as brown solid with a yield of 84%.

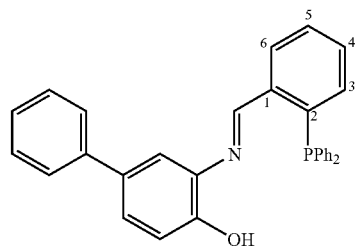

L6

The NMR results were as follows.

$^1$H NMR (500 MHz, CD$_2$Cl$_2$) δ (ppm): 6.90 (d, 1H, J$_{HH}$=8.3 Hz, H6 Phenol), 6.94 (m, 1H, H3), 7.21-7.37 (br m, 10H), 7.45 (m, 3H), 7.94 (m, 1H, H6), 8.98 (d, 1H, J$_{PH}$=3.5 Hz, CH=N).

$^{13}$C{$^1$H} NMR (125 MHz, CD$_2$Cl$_2$) δ (ppm): 115.1 (C6 phenol), 115.6 (C3 phenol), 126.9 (2C, CH ortho phenyl), 127.2 (CH para phenyl), 127.7 (C5 phenol), 129.0 (d, 4C, J$_{PC}$=11 Hz, CH meta PPh$_2$), 129.1 (2C, CH meta phenyl), 129.2 (C6), 129.3 (2C, CH para PPh$_2$), 131.2 (C5), 131.8 (d, J$_{PC}$=4 Hz, C4), 133.6 (C4 phenol), 134.3 (d, 4C, J$_{PC}$=20 Hz, CH ortho PPh$_2$), 134.9 (C3), 136.6 (C—C phenyl), 137.5 (d, 2C, J$_{PC}$=8 Hz, C ipso PPh$_2$), 138.6 (d, J$_{PC}$=21 Hz, C1), 139.0 (d, J$_{PC}$=15 Hz, C2), 140.9 (C—N), 151.9 (C—OH), 157.9 (d, J$_{PC}$=9 Hz, CH=N).

$^{31}$P{$^1$H, $^{13}$C} NMR (202 MHz, CD$_2$Cl$_2$) δ (ppm): −6.4.

Synthesis of 3-[(2-diphenylphosphino)benzylimino]-2-naphtol (L7)

The procedure was the same as that used for preparing L1 except that 159 mg of 3-amino-2-naphtol (1 mmol) were used as reagent. 346 mg of ligand L7 were obtained as green solid with a yield of 78%.

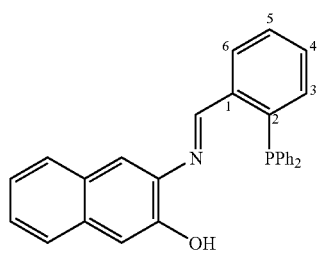

L7

The NMR results were as follows.

$^1$H NMR (500 MHz, CD$_2$Cl$_2$) δ (ppm): 6.99 (m, 1H, H3), 7.16 (s, 1H, H1 naphtol), 7.21 (td, 1H, J$_{HH}$=7.5 Hz, J$_{PH}$=1 Hz, H6 naphtol), 7.24-7.31 (br m, 12H, PPh$_2$ and OH and H7 naphtol), 7.33 (td, 1H, J$_{HH}$=7.5 Hz, J$_{PH}$=1 Hz, H4), 7.43 (s, 1H, H4 naphtol), 7.48 (td, 1H, J$_{HH}$=7.5 Hz, J$_{PH}$=1 Hz, H5), 7.58 (d, 1H, $J_{HH}$=8.2 Hz, H8 naphtol), 7.63 (d, $J_{HH}$=8.2 HZ, H5 naphtol), 7.98 (m, 1H, H6), 9.02 (d, 1H, $J_{PH}$=3.6 Hz, CH=N).

$^{13}C\{^{1}H\}$ NMR (125 MHz, $CD_2Cl_2$). δ (ppm): 109.2 (C1 naphtol), 114.1 (C4 naphtol), 123.9 (C6 naphtol), 126.4 (C8 naphtol), 126.6 (C7 naphtol), 128.3 (C5 naphtol), 128.9 (C4a naphtol), 129.0 (d, 4C, $J_{PC}$=7 Hz, CH meta $PPh_2$), 129.3 (C6), 129.4 (2C, CH para $PPh_2$), 131.4 (C5), 132.0 (d, $J_{PC}$=4 Hz, C4), 134.3 (d, 4C, $J_{PC}$=20 Hz, CH ortho $PPh_2$), 134.6 (C8a naphtol), 135.0 (C3), 137.4 (d, 2C, $J_{PC}$=8 Hz, C ipso $PPh_2$), 138.8 (C—N), 138.9 (d, $J_{PC}$=15 Hz, C2), 139.0 (d, $J_{PC}$=21 Hz, C1), 150.6 (C—OH), 159.4 (d, $J_{PC}$=8.5 Hz, CH=N).

$^{31}P\{^{1}H, C)\}$ NMR (202 MHz, $CD_2CO_2$) δ (ppm): −6.5.

Synthesis of 2-[(2-diphenylphosphino)benzylimino]-4-nitro-phenol (L8)

The procedure was the same as that used for preparing L1 except that 154 mg of 2-amino-4-nitrophenol (1 mmol) were used as reagent. 256 mg of ligand L8 were obtained as yellow solid with a yield of 58%.

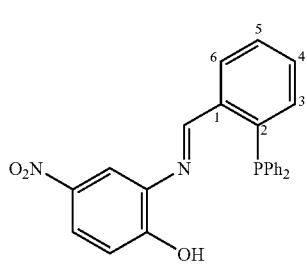

L8

The NMR results were as follows.

$^{1}H$ NMR (500 MHz, $CD_2Cl_2$) δ (ppm): 6.94 (d, 1H, $J_{HH}$=8.9 Hz, H6 Phenol), 6.98 (m, 1H, H3), 7.20 (m, 4H, H ortho $PPh_2$), 7.28 (m, OH, H meta and para $PPh_2$), 7.35 (td, $J_{HH}$=7.5 Hz, $J_{PH}$=1 Hz, H4), 7.49 (td, 1H, $J_{HH}$=7.5 Hz, $J_{PH}$=1 Hz, H5), 7.90 (m, 1H, H6), 7.95 (d, 1H, $J_{PH}$=2.5 Hz, H3 Phenol), 7.98 (dd, 1H, $J_{HH}$=8.9 Hz, $J_{PH}$=2.6 Hz, H5 Phenol), 8.15 (s, 1H, OH), 8.92 (d, 1H, $J_{PH}$=3.2 Hz, CH=N).

$^{13}C\{^{1}H\}$ NMR (125 MHz, $CD_2Cl_2$) δ (ppm): 112.6 (C3 Phenol), 115.4 (C6 Phenol), 124.7 (C5 Phenol), 129.1 (d, 4C, $J_{CP}$=7 Hz, CH meta $PPh_2$), 129.4 (C6), 129.5 (2C, CH para $PPh_2$), 131.8 (C5), 133.1 (d, $J_{CP}$=4 Hz, C4), 134.2 (d, 4C, $J_{CP}$=20 Hz, CH ortho $PPh_2$), 135.3 (C3), 136.4 (C—N), 137.1 (d, $J_{CP}$=7 Hz, C ipso $PPh_2$), 138.3 (d, $J_{CP}$=14 Hz, C2), 138.9 (d, $J_{CP}$=21 Hz, C1), 141.5 (C—$NO_2$), 157.9 (C—OH), 160.4 (d, $J_{CP}$=6 Hz, C=N).

$^{31}P\{^{1}H, ^{13}C\}$ NMR (202 MHz, $CD_2Cl_2$) δ (ppm): −5.3.

Synthesis of 2-[(2-diphenylphosphino)benzylimino]-4-chloro-phenol L9

The procedure was the same as that used for preparing L1 except that 144 mg of 2-amino-4-chlorophenol (1 mmol) were used as reagent. 285 mg of ligand L9 were obtained as ochre solid with a yield of 66%.

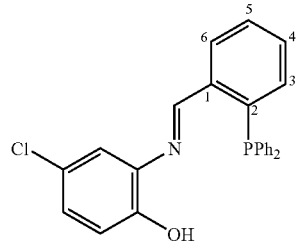

L9

The NMR results were as follows.

$^{1}H$ NMR (500 MHz, $CD_2Cl_2$) δ (ppm); 6.78 (d, 1H, $J_{HH}$=8.6 Hz, H6 Phenol), 6.95 (m, 1H, H3), 6.98 (d, $J_{PH}$=2 Hz, H3 Phenol), 7.01 (dd, $J_{HH}$=8.6 Hz, $J_{PH}$=2 Hz, H5 Phenol), 7.20 (m, 4H, H ortho $PPh_2$), 7.28 (m, 7H, H meta and para $PPh_2$ and H4), 7.45 (t, 1H, $J_{HH}$=7.5 Hz, H5), 7.89 (m, 1H, H6), 8.83 (d, 1H, $J_{PH}$=3.4 Hz, CH=N).

$^{13}C\{^{1}H\}$ NMR (125 MHz, $CD_2Cl_2$) δ (ppm): 116.4 (C6 Phenol), 116.7 (C3 Phenol), 124.9 (C—Cl), 128.6 (C5 Phenol), 129.0 (d, 4C, $J_{PC}$=7 Hz, C meta $PPh_2$), 129.3 (C6), 129.4 (2C, CH para $PPh_2$), 131.4 (C5), 132.2 (d, $J_{PC}$=4 Hz, C4), 134.2 (d, 4C, $J_{PC}$=20 Hz, CH ortho $PPh_2$), 135.1 (C3), 137.0 (C—N), 137.3 (d, 2C, $J_{PC}$=8 Hz, C ipso $PPh_2$), 138.7 (d, $J_{PC}$=15 Hz, C1), 138.8 (d, $J_{PC}$=21 Hz, C2), 151.1 (C—OH), 158.6 (d, $J_{PC}$=8 Hz, CH=N).

$^{31}P\{^{1}H, ^{13}C\}$ NMR (202 MHz, $CD_2Cl_2$) δ (ppm): −6.4.

Preparation of Complexes

Synthesis of Cr(III) Complexes 100 mg (0.26 mmol) of ligand L1 were dissolved in 5 mL of THF and cooled at a temperature of −15° C. 1 mmol of n-butyl lithium (C=1.6M in hexane) was added dropwise. The solution was stirred for 30 minutes and added to a solution of 101 mg (0.26 mmol) of $(THF)_3CrCl_3$ dissolved in 5 mL of THF. The solution was stirred at room temperature overnight. The mixture was concentrated to approximately 2 mL, and 10 mL of pentane were added. Solvents were filtered off and the solid was washed twice with pentane. The resulting solid was dried under vacuum to afford the complex A1 as a brown powder with a yield of 92%.

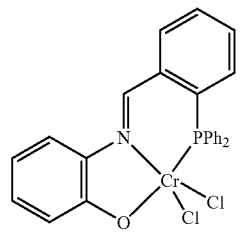

A-1

Using the same procedure, Cr(III) complex A2 was obtained from ligand L2 to afford a brown solid with a yield of 83%.

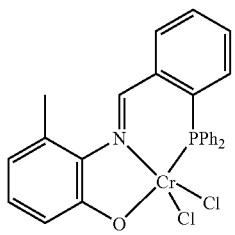

A-2

Similarly, Cr(III) complex A3 was obtained from ligand L3 to as a orange-brown solid with a yield of 90%.

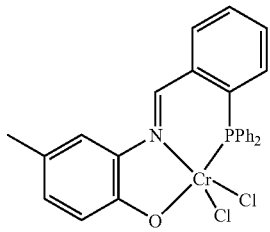

A-3

Similarly, Cr(III) complex A4 was obtained from ligand L4 to as a brown-yellow solid with a yield of 89%.

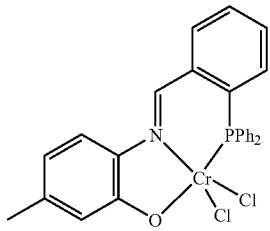

A-4

Similarly, Cr(III) complex A5 was obtained from ligand L5 to afford a brown solid with a yield of 92%.

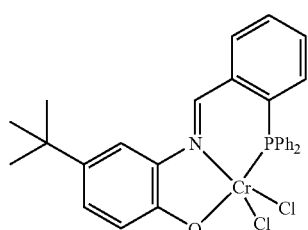

A-5

Similarly, Cr(III) complex A6 was obtained from ligand L6 to afford a brown solid with a yield of 91%.

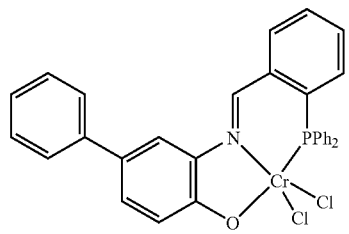

A-6

Similarly, Cr(III) complex A8 was obtained from ligand L8 to afford a brown solid with a yield of 92%.

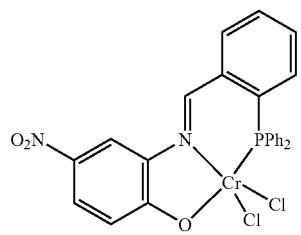

A-8

Similarly, Cr(III) complex A8 was obtained from ligand L8 to afford a brown solid with a yield of 92%.

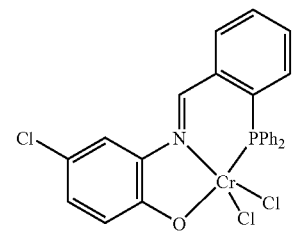

A-9

Polymerisation of Ethylene with MAO as Activating Agents

Ethylene polymerisation reactions were carried out in a 20 mL stainless steel autoclave containing a glass insert, fitted with mechanical stirring, external thermocouple and pressure gauge and controlled by a computer. In a typical reaction run, the temperature was set to the desired value (50 or 80° C.) and 4 mL of dry solvent (toluene or n-heptane) were introduced into the reactor under nitrogen flow. In a argon-filled glove box, about 4 mg (5 μmol) of the appropriate catalyst were weighted, activated with methylaluminoxane (MAO) (30% wt in toluene) in an appropriate amount to obtain a ratio [Al]:[M] of 2000, and the resulting active complex was diluted with toluene to obtain a final volume of 2 mL. 200 μL of the solution of activated catalyst were placed inside the reactor. The injection loop was rinsed with 800 μL of solvent. The ethylene pressure was raised to 15 bars and continuously fed into the reactor. After either 1 hour or an ethylene consumption of 12 mmol, the reactor was cooled down and depressurized, then the reaction was quenched with isopropanol and the solution was analysed by gas chromatography. The gas chromatographic (GC) analysis of the reaction products was performed on a Trace GC apparatus with a Petrocol capillary column (methyl silicone, 100 m long with i.d. of 0.25 mm and film thickness of 0.5 μm) working at a temperature of 35° C. for 15 min and then heating at a rate of 5° per minute up to a temperature of 250° C. The results for the polymerisation of ethylene with MAO are displayed in Tables I for a polymerisation temperature of 50° C. and in Table II for a polymerisation temperature of 80° C.

TABLE I

| Run | Complex | m PE (mg) | Activity (kg/mol/h) | DSC Tm (° C.) | DSC ΔH (J·g$^{-1}$) |
|---|---|---|---|---|---|
| 1 | A1 | 45 | 88 | 133.1 | 167.9 |
| 2 | A2 | 48 | 93 | 134.7 | 161.5 |
| 3 | A3 | 107 | 202 | 131.2 | 50.0 |
| 4 | A4 | 55 | 107 | 131.0 | 41.9 |
| 5 | A5 | 62 | 112 | 133.1 | 141.5 |
| 6 | A6 | 80 | 156 | 133.2 | 106.3 |
| 7 | A8 | 30 | 58 | 134.5 | 134.6 |
| 8 | A9 | 33 | 61 | 134.2 | 162.5 |
| 9 | A1 | 22 | 43 | / | / |
| 10 | A2 | 25 | 50 | 133.8 | 139.0 |
| 11 | A3 | 10 | 21 | 132.3 | 103.0 |
| 12 | A4 | 22 | 44 | 130.6 | 80.5 |
| 13 | A5 | 36 | 67 | 131.1 | 108.9 |
| 14 | A6 | 23 | 45 | / | / |
| 15 | A8 | 9 | 15 | / | / |
| 16 | A9 | 12 | 20 | 131.6 | 157.5 |

All Reactions were performed with 0.5 μmol of catalyst dissolved in 5 mL of solvent, at a temperature of 50° C. and with an ethylene pressure of 15 bars. The amount of activating agent (MAO) was adjusted to yield a ratio [Al]:[Cr] of 2000. Runs 1 to 8 were performed in toluene, and runs 9 to 16 were performed in n-heptane.

Activities are expressed in kg of polyethylene per mol of Cr per hour.

Most of the obtained polymers were insoluble in hot trichlorobenzene and could not be characterised by GPC.

All Reactions were performed as in the previous runs except that the polymerisation temperature was of 80° C.

Runs 17 to 24 were performed in toluene, runs 25 to 32 were performed in n-heptane.

Activities are expressed in kg of ethylene consumed per mol of Cr per hour.

All percentages of C4, C6, >C6, and α-C2n in C2n were calculated by GC analysis.

Polymerisation of Ethylene with Et$_2$AlCl as Activating Agent.

The procedure was the same as that described above with MAO except that the catalyst was activated with an appropriate amount of diethylaluminum chloride (Et$_2$AlCl, 1M in hexanes). The polymerisation results are displayed in Table III.

TABLE III

| Complex | [Al]:[Cr] | m PE (mg) | Activity (kg/mol/h) | DSC Tm (° C.) | DSC ΔH (J·g$^{-1}$) |
|---|---|---|---|---|---|
| A6 | 500 | 21 | 108 | 133.3 | 139.6 |
| A6 | 1000 | 50 | 226 | 129.7 | 154.2 |
| A6 | 1500 | 55 | 187 | 134.1 | 111.8 |
| A6 | 2000 | 18 | 122 | 125.2 | 164.5 |

All reactions were performed with 0.5 μmol of catalyst dissolved in 5 mL of toluene, at a temperature 50° C., under an ethylene pressure of 15 bars and with Et$_2$AlCl as activating agent.

Activities are expressed in kg of ethylene consumed per mol of Cr per hour.

The obtained polymers were insoluble in hot trichlorobenzene and could not be characterised by GPC.

No activity was measured when the solvent was n-heptane.

TABLE II

| Run | Complex | m PE (mg) | Activity (kg/mol/h) | % C4 Total | % α-C4 | % C6 Total | % α-C6 | % > C6 | Tm (° C.) |
|---|---|---|---|---|---|---|---|---|---|
| 17 | A1 | 13 | 25 | trace C4 to C14 | | | | | 131.7 |
| 18 | A2 | 19 | 74 | trace C4 to C10 | | | | | 132.3 |
| 19 | A3 | 11 | 37 | trace C4 to C8 | | | | | 132.5 |
| 20 | A4 | 24 | 36 | trace C4 to C8 | | | | | 130.1 |
| 21 | A5 | 19 | 94 | 15 | 97 | 21 | 80 | 65 | / |
| 22 | A6 | 15 | 182 | 14 | 97 | 20 | 82 | 66 | 128.2 |
| 23 | A8 | 22 | 61 | trace C4 to C12 | | | | | / |
| 24 | A9 | 20 | 137 | 15 | 97 | 20 | 82 | 65 | / |
| 25 | A1 | 7 | 14 | no oligomer-only PE | | | | | / |
| 26 | A2 | 14 | 49 | no oligomer-only PE | | | | | / |
| 27 | A3 | 3 | 16 | no oligomer-only PE | | | | | / |
| 28 | A4 | 6 | 17 | no oligomer-only PE | | | | | / |
| 29 | A5 | 9 | 32 | no oligomer-only PE | | | | | 131.2 |
| 30 | A6 | 10 | 47 | no oligomer-only PE | | | | | 130.8 |
| 31 | A8 | 10 | 39 | no oligomer-only PE | | | | | 131.3 |
| 32 | A9 | 4 | 30 | no oligomer-only PE | | | | | / |

The invention claimed is:
1. An active catalyst system comprising:
a) a metallic complex of formula III

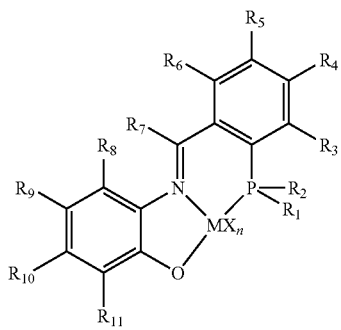

wherein $R_1$, $R_2$, $R_3$, $R_4$, $R_5$, $R_6$, $R_7$, $R_8$, $R_9$, $R_{10}$, $R_{11}$ are each independently selected from hydrogen, unsubstituted or substituted hydrocarbyl having from 1 to 20 carbon atoms, or inert functional group and wherein two or more of those groups can themselves be linked together to form further ring or rings,
wherein M is a metal Group 3 to 9 of the Periodic Table,
wherein each X is the same or different and is selected from halogen, substituted or unsubstituted hydrocarbyl having from 1 to 20 carbon atoms, substituted or unsubstituted aryloxy or alkoxy, and wherein (n+1) is the valence of M;
b) an activating agent; and
c) an optional cocatalyst.

2. The active catalyst system of claim 1 wherein M is Ti, Zr, Ht, V, Cr, Mn, Fe, Co, or rare earths.

3. The active catalyst system of claim 1 wherein $R_1$ and $R_2$ are the same or different and are unsubstituted or substituted alkyl groups, unsubstituted or substituted aryl groups, or unsubstituted or substituted cycloalkyl groups having at most 12 carbon atoms.

4. The active catalyst system of claim 3 wherein $R_1$ and $R_2$ are the same and are unsubstituted phenyl groups.

5. The active catalyst system of claim 1 wherein $R_3$, $R_4$, $R_5$, $R_6$ and $R_7$, are the same and are hydrogen.

6. The active catalyst system of claim 1 wherein $R_8$, $R_{10}$ and $R_{11}$ are hydrogen or methyl, wherein $R_9$ is hydrogen, methyl, tert-butyl, phenyl, nitro or chlorine.

7. The active catalyst system of claim 1 wherein X is a halogen.

8. A process for preparing the active catalyst system of claim 1 that comprises the steps of:
a) providing a ligand of formula I

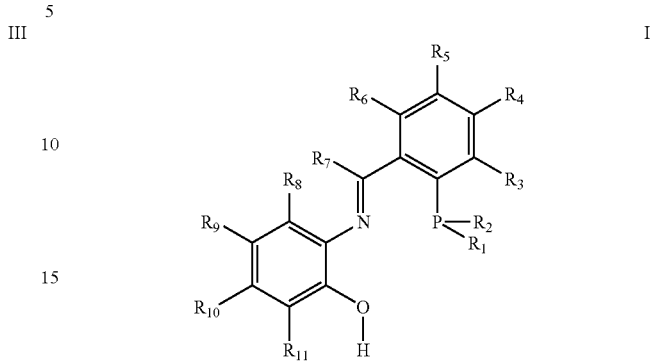

b) complexing the ligand of step a) with a metallic salt $MX_{n+1}$ in a solvent;
c) retrieving the metallic complex of formula III;
d) activating the metallic complex of step c) with an activating agent having an ionising action or with an activating support;
e) optionally adding a cocatalyst;
retrieving an active oligomerisation or polymerisation catalyst system,
wherein $R_1$, $R_2$, $R_3$, $R_4$, $R_5$, $R_6$, $R_7$, $R_8$, $R_9$, $R_{10}$, $R_{11}$, M, X and n are as described in claim 1.

9. The process of claim 8 wherein the activating support is silica impregnated with an activating agent.

10. The process of claim 8 wherein the activating agent is aluminiumalkyl or aluminoxane.

11. The process of claim 8 wherein the cocatalyst is triethylaluminium, triisobutylaluminum, tris-n-octylaluminium, tetraisobutyldialuminoxane or diethyl zinc.

12. A method for the oligomerisation or the homo- or co-polymerisation of ethylene and alpha-olefins that comprises the steps of:
a) injecting the active catalyst system of claim 1 into the reactor;
b) injecting the monomer and optional comonomer;
c) maintaining under polymerisation conditions;
d) retrieving the oligomers and/or polymer.

13. The method of claim 12 wherein the monomer is ethylene or propylene.

* * * * *